United States Patent [19]
Taylor

[11] 3,939,837
[45] Feb. 24, 1976

[54] DISPOSABLE DIAPER WITH FIT IMPROVING MEANS
[75] Inventor: Glenn N. Taylor, Cary, Ill.
[73] Assignee: The Kendall Company, Walpole, Mass.
[22] Filed: Feb. 4, 1974
[21] Appl. No.: 439,100

[52] U.S. Cl. .............................................. 128/287
[51] Int. Cl.² ................................... A61F 13/16
[58] Field of Search ....... 128/284, 286, 287, 132 D, 128/290, 155–157, 165, 171, 327

[56] References Cited
UNITED STATES PATENTS

| | | | |
|---|---|---|---|
| 2,407,735 | 9/1946 | Beckerman | 128/157 |
| 3,368,562 | 2/1968 | Vogt | 128/284 |
| 3,422,815 | 1/1969 | Jamison | 128/284 |
| 3,572,342 | 3/1971 | Lindquist et al. | 128/287 |
| 3,606,887 | 9/1971 | Roeder | 128/290 R |
| 3,800,796 | 4/1974 | Jacob | 128/284 |
| 3,815,602 | 6/1974 | Johns et al. | 128/287 |

Primary Examiner—Robert W. Michell
Assistant Examiner—Rick Opitz

[57] ABSTRACT

A folded disposable diaper having lateral margins, a front section, and a back section. The folded configuration places the diaper lateral margins into contact with each other and those margins are releasably secured to each other thereby permitting the temporary retention of the front section in the folded configuration while the back section is unfolded for application of the diaper to an infant.

4 Claims, 3 Drawing Figures

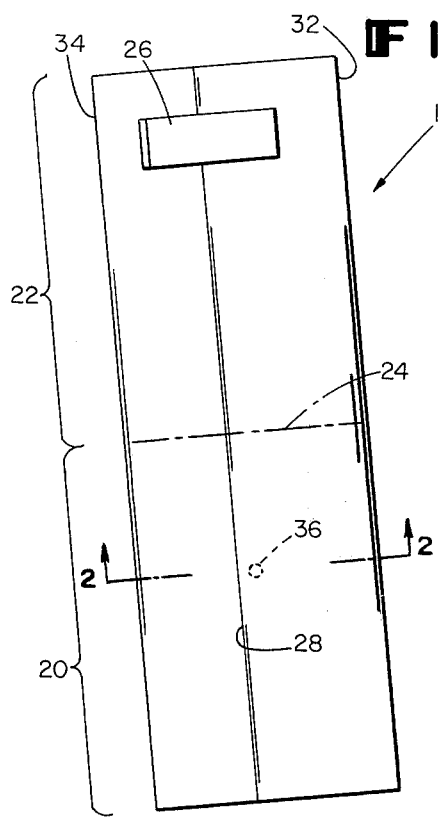
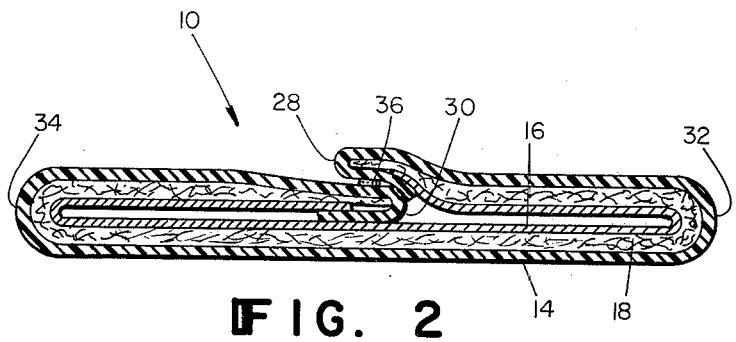
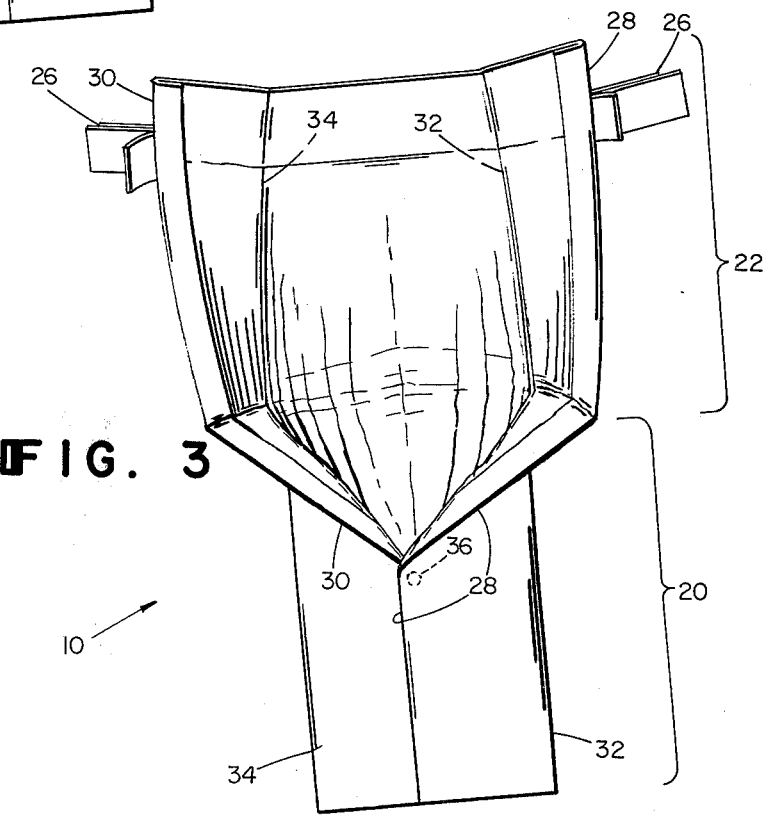

DISPOSABLE DIAPER WITH FIT IMPROVING MEANS

BACKGROUND OF THE INVENTION

This invention relates to disposable diapers.

In recent years there have appeared a number of disposable diapers which provide a tapering of the diaper in the crotch portion thereof in order to achieve a better fit of the diaper on an infant. In each such diaper, however, the taper is built into the diaper during its manufacture. This typically has increased the difficulty of manufacture and has left the consumer with little or no choice as to whether or not to use the tapering feature and as to the degree of taper which is desirable for a particular infant in particular circumstances.

Summary of the Invention

It is a principal object of the present invention to provide a diaper construction which permits a tapered configuration for the diaper, as applied to an infant, while minimizing manufacturing complexity and permitting a degree of freedom for the consumer to adjust the diaper shape for a particular infant.

The invention features a disposable diaper having lateral margins and having front and rear sections on opposite sides of a longitudinal midpoint. The diaper is folded into a configuration in which the lateral margins are at least in contact, and preferably somewhat overlapping. The lateral margins are releasably secured to each other in the diaper front section, whereby the front section may be temporarily retained in the folded configuration while the back section is unfolded for application of the diaper to an infant.

In preferred embodiments of the invention an adhesive is employed to releasably secure the lateral margins; the lateral margins are releasably secured to each other at a single location; and that single location is between about two inches to about four inches along the diaper margins from the diaper midpoint.

BRIEF DESCRIPTION OF THE DRAWING

Other objects, features, and advantages of the invention will appear from the following description of a particular preferred embodiment taken together with the accompanying drawing in which:

FIG. 1 is a plan view of a diaper constructed according to the present invention;

FIG. 2 is a view taken at 2—2 of FIG. 1; and

FIG. 3 is a plan view of the diaper of FIG. 1 as partially unfolded for application to an infant.

DETAILED DESCRIPTION OF A PARTICULAR PREFERRED EMBODIMENT

Referring to the drawing, a diaper 10 has a generally conventional construction with an outer water impervious plastic backing sheet 14, an inner water pervious liner 16, and an absorbent body 18 therebetween. The diaper has front and back sections 20, 22 on opposite sides of the longitudinal midpoint of the diaper (indicated at reference line 24). Conventional tape fastener units 26 are provided in the back section 22 adjacent the diaper lateral margins 28, 30.

The diaper is folded along longitudinal fold lines 32, 34. The lateral location of the fold lines 32, 34 with respect to the associated lateral margins 28, 30 are chosen such that the margins 28, 30 slightly overlap, as best seen in FIG. 2. In the front section 20 of the diaper, the overlapping marginal portions are releasably secured to each other, as by a spot of adhesive 36.

This diaper construction assists in the application of the diaper to an infant, and achieves a taper in the diaper as applied to the infant. The diaper is presented to the consumer in the configuration shown in FIG. 1. (Although for packaging the diaper might be folded about the reference line 24, it would be flipped open to the configuration of FIG. 1 by the consumer as it was taken from the package and placed on a surface preparatory to application to an infant.) The back section 22 may then be unfolded about the fold lines 32, 34 to achieve the configuration shown in FIG. 3. In this configuration, most of the back section 22 is fully opened for placement of the diaper around the infant. Portions of both sections 20, 22 adjacent the reference line 24 are constrained by the adhesive 36 to a tapered configuration in the longitudinally central portion (i.e., the crotch portion) of the diaper 10. The infant is then placed upon the opened part of the diaper. The weight of the infant will be sufficient to retain the tapering caused by the spot of adhesive 36 even though the bond produced by the adhesive is severed and the front section unfolded and placed around the infant.

While the precise location of the spot of glue 36 is not critical, it has been found that for a diaper having an overall length of about 17 inches, the spot of glue 36 may be desirably located between about two and about four inches from the reference line 24. Preferably, the glue spot 36 is spaced from the reference line 24 a distance approximately equal to one sixth the total length of the diaper.

While a particular preferred embodiment of the invention has been illustrated in the accompanying drawing and described in detail herein, other embodiments are within the scope of the invention and the following claims.

I claim:

1. In a generally rectangular disposable diaper comprising an outer water impervious backing sheet, an inner water pervious liner and an absorbent body therebetween and having opposite lateral margins and having a front section and a back section on opposite sides of a longitudinal midpoint of the diaper, the improvement wherein said diaper is folded into a configuration with said lateral margins in contact, said lateral margins being releasably adhesively secured to each other only in said diaper front section at a location between from about two inches to about four inches along said margins from said diaper midpoint, whereby said front section may be temporarily retained in said folded configuration while said back section is unfolded for application of the diaper to an infant.

2. A disposable diaper as claimed in claim 1 wherein said lateral margins are releasably secured to each other at a single location.

3. In a generally rectangular disposable diaper having a predetermined length and comprising an outer water impervious backing sheet, an inner water pervious liner and an absorbent body therebetween and having opposite lateral margins and having a front section and a back section on opposite sides of a longitudinal midpoint of the diaper, the improvement wherein said diaper is folded into a configuration with said lateral margins in contact, said lateral margins being releasably adhesively secured to each other only in said diaper front section at a location spaced from said diaper midpoint along said margins a distance approximately equal to one sixth said predetermined length, whereby said front section may be temporarily retained in said folded configuration while said back section is unfolded for application of the diaper to an infant.

4. A disposable diaper as claimed in claim 3 wherein said lateral margins are releasably secured to each other at a single location.

* * * * *